US011389076B2

(12) United States Patent
Maeda et al.

(10) Patent No.: US 11,389,076 B2
(45) Date of Patent: Jul. 19, 2022

(54) BIOMAGNETIC MEASUREMENT SYSTEM AND BIOMAGNETIC MEASUREMENT METHOD

(71) Applicants: Ryoh Maeda, Kanagawa (JP); Yuki Miyano, Tokyo (JP)

(72) Inventors: Ryoh Maeda, Kanagawa (JP); Yuki Miyano, Tokyo (JP)

(73) Assignee: Ricoh Company, Ltd., Tokyo (JP)

( * ) Notice: Subject to any disclaimer, the term of this patent is extended or adjusted under 35 U.S.C. 154(b) by 205 days.

(21) Appl. No.: 16/806,021

(22) Filed: Mar. 2, 2020

(65) Prior Publication Data

US 2020/0281499 A1    Sep. 10, 2020

(30) Foreign Application Priority Data

Mar. 8, 2019 (JP) .............................. JP2019-043075

(51) Int. Cl.
*A61B 5/05* (2021.01)
*A61B 5/00* (2006.01)

(52) U.S. Cl.
CPC .............. *A61B 5/05* (2013.01); *A61B 5/0048* (2013.01); *A61B 5/7214* (2013.01); *A61B 2562/18* (2013.01)

(58) Field of Classification Search
None
See application file for complete search history.

(56) References Cited

U.S. PATENT DOCUMENTS

| 7,899,547 B1* | 3/2011 | Emadi ................... A61N 1/323 607/62 |
| 2016/0091581 A1* | 3/2016 | Kolandaivelu .. G01R 33/56536 324/322 |
| 2018/0242865 A1* | 8/2018 | Yamagata ................ A61B 5/24 |
| 2019/0183376 A1 | 6/2019 | Sato et al. |

FOREIGN PATENT DOCUMENTS

| JP | 2017-051600 | 3/2017 |
| JP | 2017-221515 | 12/2017 |

OTHER PUBLICATIONS

Jan Nilsson et al., "Stimulus Artifact Compensation Using Biphasic Stimulation", Muscle & Nerve, Jun. 1988, pp. 597-602.
Kensuke Sekihara et al., "Dual signal subspace projection (DSSP): a novel algorithm for removing large interference in biomagnetic measurements", Journal of Neural Engineering, Apr. 11, 2016, pp. 1-19.

* cited by examiner

*Primary Examiner* — Yi-Shan Yang
(74) *Attorney, Agent, or Firm* — IPUSA, PLLC

(57) ABSTRACT

A biomagnetic measurement system includes a magnetism measurement apparatus configured to measure a magnetism of a target; and an electrical stimulation apparatus configured to apply a stimulation current to the target. The magnetism measurement apparatus includes a confirming unit configured to confirm a magnitude of an artifact caused by the stimulation current. The electrical stimulation apparatus is configured to output a compensation current for reducing the artifact after the stimulation current is output, based on information from the confirming unit.

7 Claims, 9 Drawing Sheets

BIOMAGNETIC MEASUREMENT SYSTEM AND BIOMAGNETIC MEASUREMENT METHOD

CROSS-REFERENCE TO RELATED APPLICATION

The present application is based on and claims priority under 35 U.S.C. § 119 to Japanese Patent Application No. 2019-043075, filed on Mar. 8, 2019, the contents of which are incorporated herein by reference in their entirety.

BACKGROUND OF THE INVENTION

1. Field of the Invention

The present invention relates to a biomagnetic measurement system and a biomagnetic measurement method.

2. Description of the Related Art

In a biomagnetic measurement system that measures extremely weak magnetism generated by nerves, the brain, and muscles, there is a method of electrically stimulating nerves as a means of generating stable biomagnetism. However, artifacts are generated due to electrical stimulation, and the artifacts greatly disturb the biomagnetic waveform, and, therefore, it is necessary to take some kinds of measures to reduce the artifacts. For example, a signal processing technique such as Dual Signal Subspace Project (DSSP) is known to reduce artifacts (see, for example, Non-patent Document 1).

Non-patent Document 1: Kensuke Sekihara, "Dual signal subspace projection (DSSP): A novel algorithm for removing large interference in biomagnetic measurements", *Journal of Neural Engineering*, Apr. 11, 2016

SUMMARY OF THE INVENTION

According to one aspect of the present invention, there is provided a biomagnetic measurement system including a magnetism measurement apparatus configured to measure a magnetism of a target; and an electrical stimulation apparatus configured to apply a stimulation current to the target, wherein the magnetism measurement apparatus includes a confirming unit configured to confirm a magnitude of an artifact caused by the stimulation current, and wherein the electrical stimulation apparatus is configured to output a compensation current for reducing the artifact after the stimulation current is output, based on information from the confirming unit.

DETAILED DESCRIPTION OF THE PREFERRED EMBODIMENTS

Figure 1:
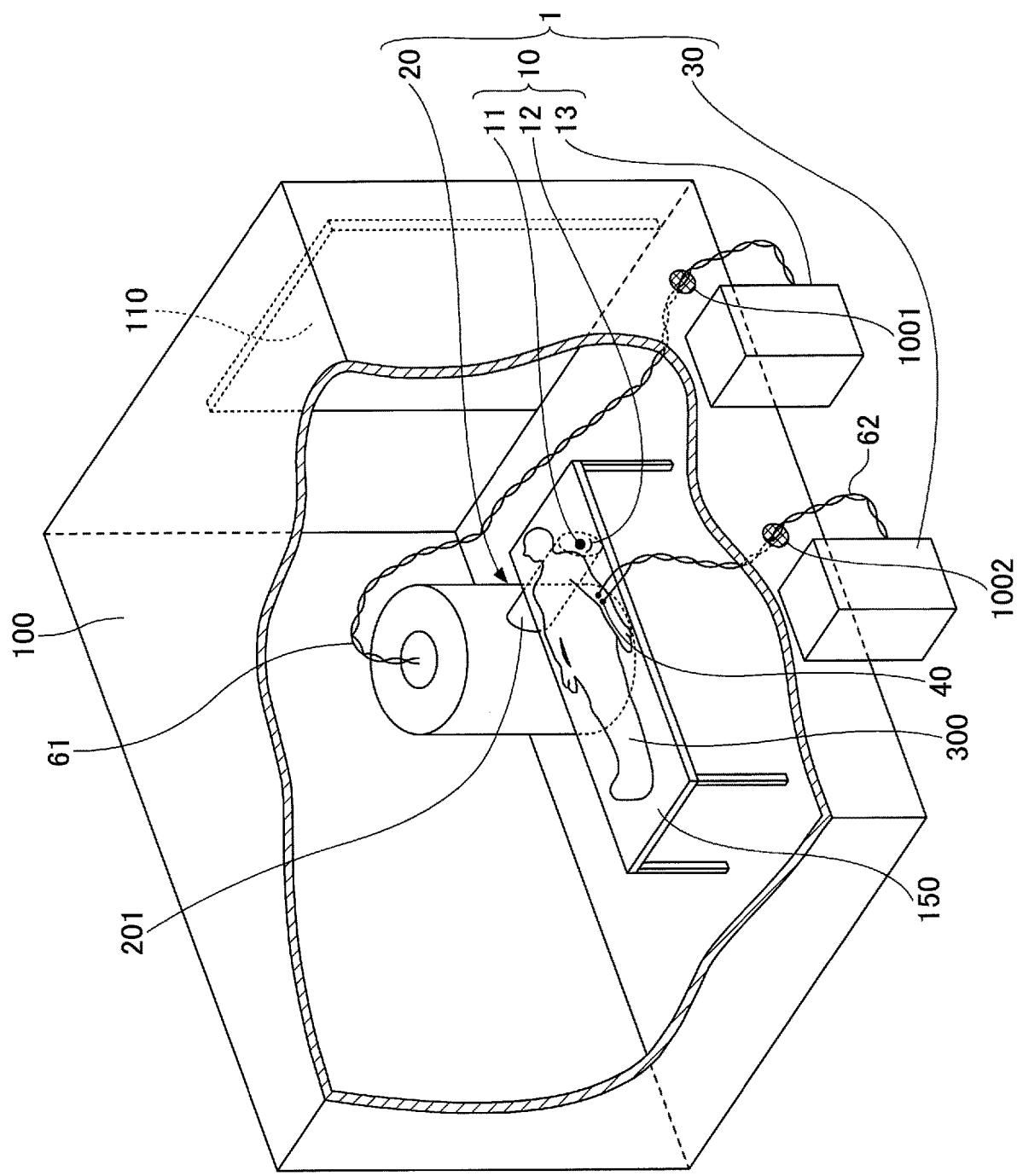
FIG. 1 is a diagram illustrating a biomagnetic measurement system according to an embodiment of the present invention.

The artifact reduction technique using a signal processing technique has been problematic because the magnetic signals generated by a living body are distorted.

A problem to be addressed by an embodiment of the present invention is to provide a biomagnetic measurement system that is capable of physically reducing artifacts.

Hereinafter, embodiments will be described with reference to the drawings. Note that in the drawings, the same elements are denoted by the same reference numerals and overlapping descriptions may be omitted.

First Embodiment (Biomagnetic Measurement System)

Figure 2:
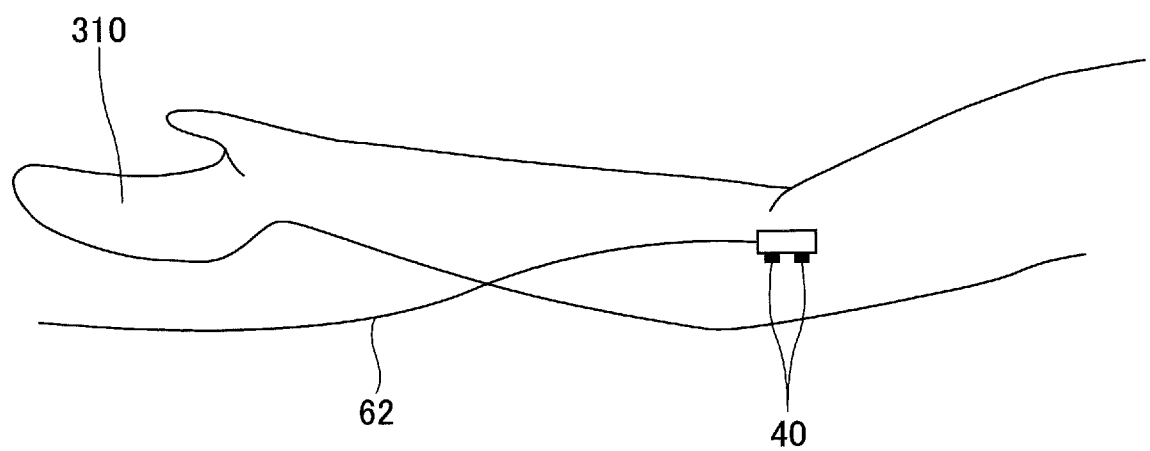
FIG. 2 is an enlarged view of the vicinity of an electrode attached to a subject according to an embodiment of the present invention.

FIG. 1 is a diagram illustrating a biomagnetic measurement system according to the present embodiment. FIG. 2 is an enlarged view of the vicinity of an electrode attached to a subject.

Referring to FIG. 1, a biomagnetic measurement system 1 includes a magnetic measurement apparatus 10, a low-temperature container 20, and an electrical stimulation apparatus 30, as the main elements.

The magnetic measurement apparatus 10 is an apparatus for measuring the magnetism of a living body (a target), and includes a magnetic sensor 11, a sensor holding device 12, and a recording device 13.

The magnetic sensor 11 detects biomagnetism. The biomagnetism is extremely weak, typically approximately several tens of fT to several tens of pT, and, therefore, a magnetic sensor with high sensitivity is used as the magnetic sensor 11. Examples of the magnetic sensor 11 include a superconducting quantum interference device (SQUID), an atomic magnetic sensor, a diamond nitrogen-vacancy center, a magnetoresistive sensor, a magnetic impedance sensor, and the like. In the present embodiment, as an example, a three-axis SQUID of the first-order gradiometer configuration is used as the magnetic sensor 11.

In the biomagnetic measurement system 1, a plurality of the magnetic sensors 11 of the magnetic measurement apparatus 10 are disposed at desired positions, and the sensor holding device 12 is used to prevent the positions of the magnetic sensors 11 relative to the measurement positions from being misaligned. In the present embodiment, the sensor holding device 12 has an insulation mechanism to cool the magnetic sensors 11 to a temperature at which the magnetic sensors 11 become in a superconductive state.

Figure 3:
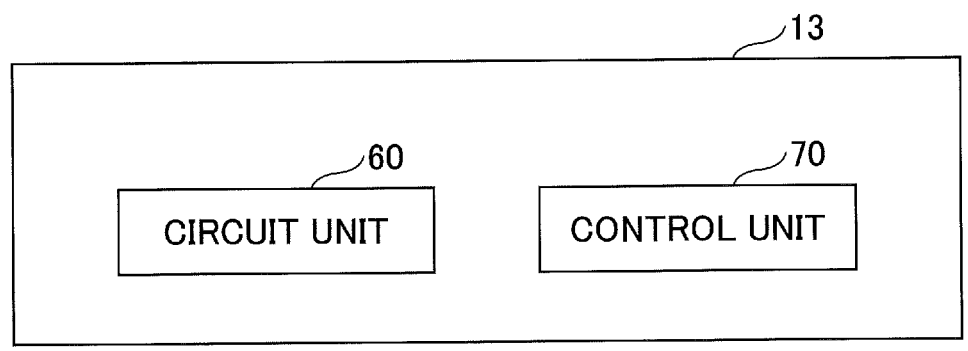
FIG. 3 is a diagram illustrating an example of a schematic configuration of a recording device included in a biomagnetic measurement system according to an embodiment of the present invention.

The output from the magnetic sensor 11 is transmitted to and recorded in the recording device 13. As illustrated in FIG. 3, the recording device 13 includes a circuit unit 60 and a control unit 70. The circuit unit 60 includes, for example, a Flux Locked Loop (FLL) circuit for driving the magnetic sensor 11, a signal processing circuit, an analog-to-digital conversion circuit, a data recording circuit, and the like.

A portion of the biomagnetic measurement system 1 is disposed within a magnetic shielding room 100. The magnetic shielding room 100 is used to measure the biomagnetism, which is a weak magnetic field generated from a living body. The magnetic shielding room 100 can be formed, for example, by laminating a plate material made of permalloy and the like as a high magnetic permeability material and a plate material made of an electrical conductor such as copper, aluminum, and the like.

The magnetic shielding room 100 has an internal space having a size of approximately 2.5 m×3.0 m×2.5 m, for example, and is provided with a door 110 for allowing for transporting equipment and for the entry and exit of people. The door 110 may be formed by laminating a plate material made of permalloy and the like as a high magnetic permeability material and a plate material made of an electrical conductor such as copper, aluminum, and the like, similar to other portions of the magnetic shielding room 100.

Note that in the present specification, a high magnetic permeability material refers to a material having a relative magnetic permeability that is greater than 1000. Examples of such materials include iron, nickel, and cobalt as a single substance, an alloy thereof (including an amorphous alloy, a powder, and nanoparticles), ferrites, and the like, other than permalloy.

Hereinafter, the biomagnetic measurement system 1 and the peripheral portions thereof will be described in more detail. In the magnetic shielding room 100, a bed 150 is installed. Further, in the magnetic shielding room 100, the low-temperature container 20 is installed, and a signal line 61 used for measurement, control, and the like is attached to the low-temperature container 20. The signal line 61 is formed of a twisted cable and the like to reduce magnetic noise, and is drawn out of the magnetic shielding room 100 through a hole 1001 in the magnetic shielding room 100, and is connected to the recording device 13.

When performing measurement by using the biomagnetic measurement system 1, a subject 300 lies face up on the bed 150 placed in the magnetic shielding room 100, and the biomagnetism is measured while the subject 300 is at rest. By performing the measurement while the subject is at rest, not only is it less burdensome to the subject 300, but it is also possible to reduce misalignment with the measurement apparatus caused by unnecessary movements of the subject 300, and to reduce magnetic noise and the like from muscles caused by muscle tension.

The low-temperature container 20 is also referred to as a dewar, and holds liquid helium required for cryogenic operations of the magnetic sensor 11 for detecting the magnetism generated from a living body. The low-temperature container 20 includes, for example, a protrusion 201 suitable for measuring the biomagnetism, and the magnetic sensor 11 is placed in the liquid helium within the protrusion 201.

By moving the protrusion 201, having the magnetic sensor 11 placed therein, close to the cervical spine of the subject 300 from under the subject 300 facing up on the bed 150, biomagnetic measurement can be performed while the magnetic sensor 11 is in close proximity to the measurement region.

When measuring the biomagnetism, it is necessary to deliberately cause neuronal activity by electrical stimulation. Thus, as illustrated in FIG. 2, an electrode 40 is attached to a portion 310 of the body of the subject 300 and electrical stimulation is applied. The electrode 40 includes two electrodes, an anode and a cathode, and is attached to the skin at a portion of the subject 300 where signals can be efficiently applied to the median nerve, etc., of the elbow joint portion or the knee joint portion of the subject 300.

To the electrode 40, a signal line 62 is attached for transmitting stimulation. The signal line 62 is formed by a twisted cable and the like to reduce magnetic noise. The signal line 62 is drawn out of the magnetic shielding room 100 through a hole 1002 in the magnetic shielding room 100 and is coupled to the electrical stimulation apparatus 30 located outside of the magnetic shielding room 100.

The electrical stimulation apparatus 30 is an apparatus that applies a stimulation current and the like to a living body. The electrical stimulation apparatus 30 includes the electrode 40 that can be attached to the region to which electrical stimulation is desired to be applied, and a pulsed stimulation current can be passed between the anode and cathode of the electrode 40 to cause a neural activity in the subject 300.

Figure 4:
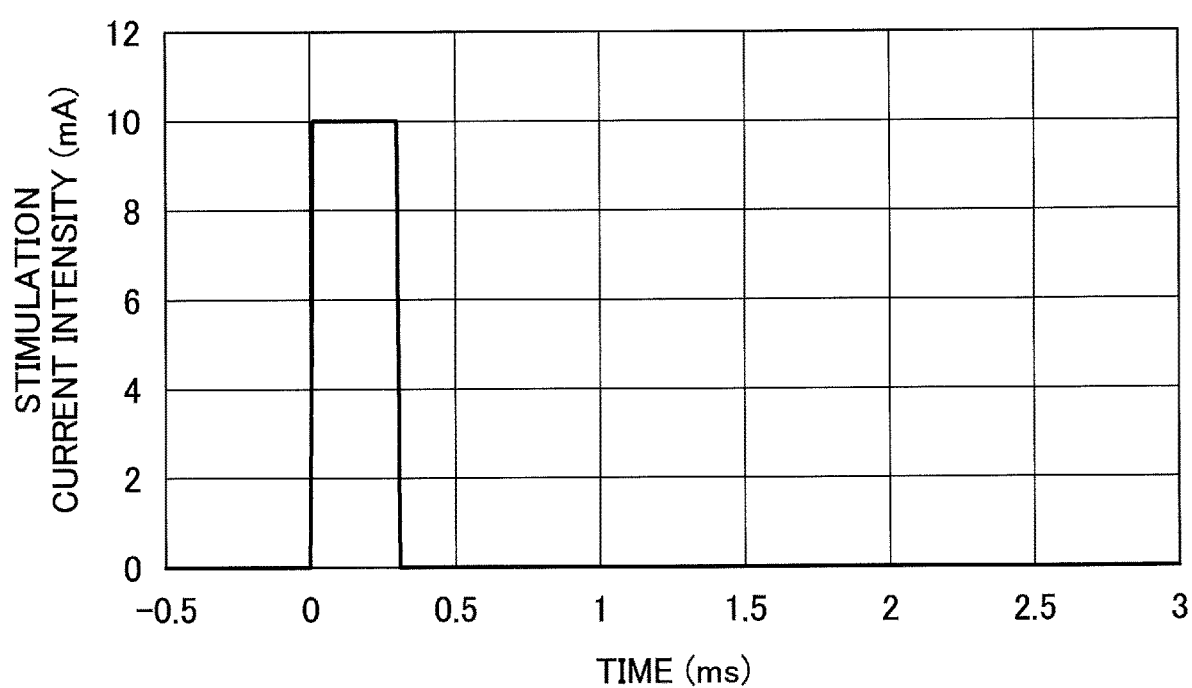
FIG. 4 is a diagram illustrating an example of a waveform of a stimulation current according to an embodiment of the present invention.

Specifically, for example, in a state where the electrode 40 is mounted at the position as illustrated in FIG. 2, the electrical stimulation apparatus 30 generates a pulsed stimulation current, for example, as illustrated in FIG. 4, during biomagnetic measurement, and applies the generated stimulation current between the anode and the cathode of the electrode 40. At this time, the stimulation current is applied periodically at a frequency of, for example, approximately several Hz to 20 Hz. The biomagnetism induced by the electrical stimulation by the electrical stimulation apparatus 30 is detected by the magnetic sensor 11, but the detected biomagnetism signal is of a small amplitude, and, therefore, the biomagnetism signals are summed and averaged in synchronization with the electrical stimulation, for example.

Figure 5:
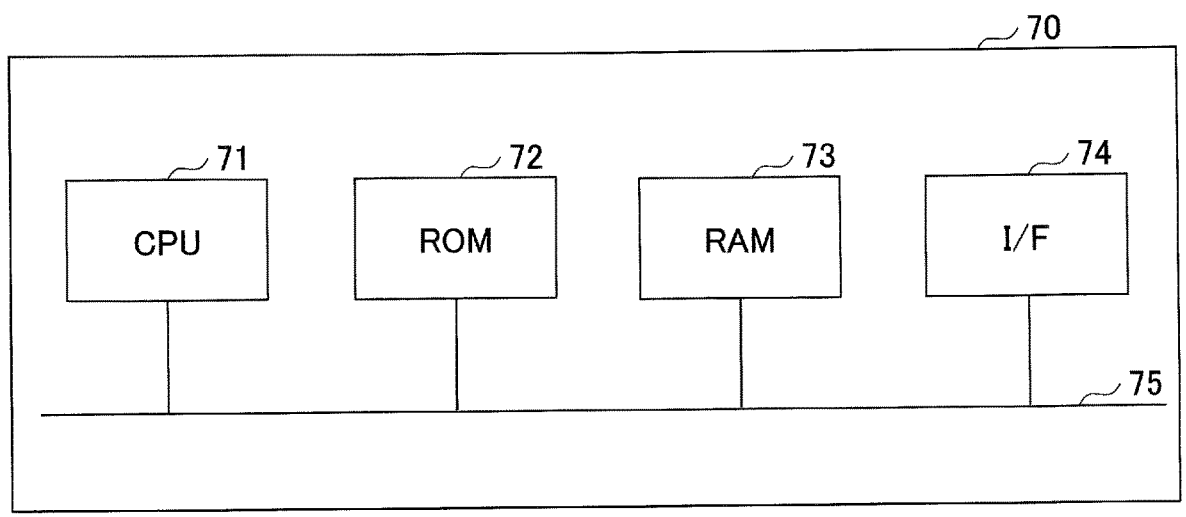
FIG. 5 is an example of a hardware block diagram of a control unit of a recording device included in the biomagnetic measurement system according to an embodiment of the present invention.

FIG. 5 is an example of a hardware block diagram of the control unit 70 of the recording device 13 included in the biomagnetic measurement system 1. As illustrated in FIG. 5, the control unit 70 includes a central processing unit (CPU) 71, a read-only memory (ROM) 72, a random access memory (RAM) 73, an interface (I/F) 74, and a bus line 75 as the main elements. The CPU 71, the ROM 72, the RAM 73, and the I/F 74 are coupled to each other via the bus line 75. The control unit 70 is coupled to various control targets, various sensors, and the like. The control unit 70 may include other hardware blocks according to need.

The CPU 71 controls each function of the control unit 70. The ROM 72, which is a storage means, stores programs that are executed by the CPU 71 to control each function of the control unit 70, and various kinds of information. The RAM 73, which is a storage means, is used as a work area and the like of the CPU 71. Further, the RAM 73 can temporarily store predetermined information. The I/F 74 is an interface for coupling with other devices and the like; for example, the I/F 74 is coupled to an external network.

The control unit 70 may be a processor programmed to execute each function by software, such as a processor implemented by an electronic circuit, or an Application Specific Integrated Circuit (ASIC), a digital signal processor (DSP), a field programmable gate array (FPGA), a System on a chip (SOC), or a Graphics Processing Unit (GPU) designed to execute a predetermined function. Further, the control unit 70 may be a circuit module and the like.

Figure 6:
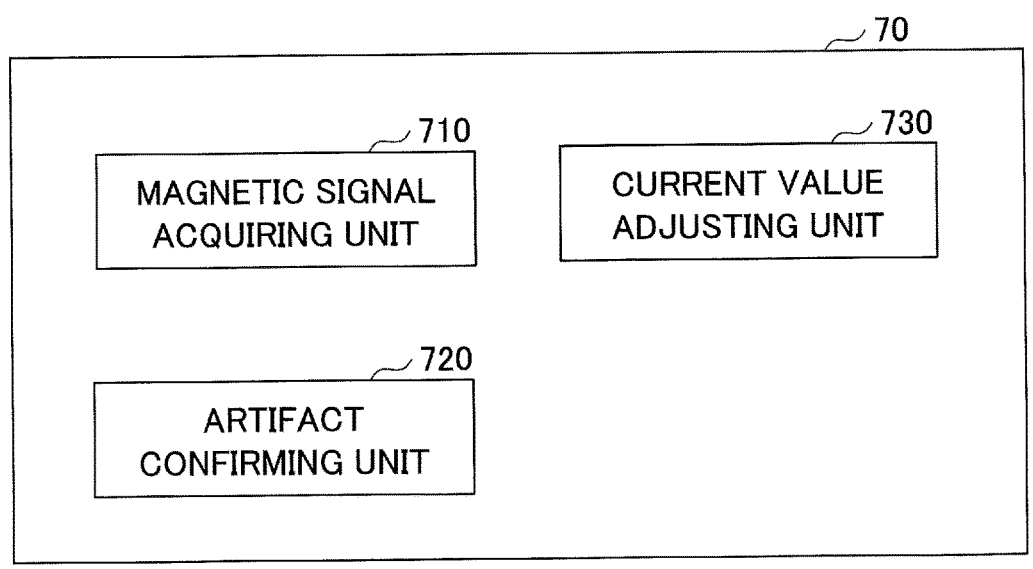
FIG. 6 is an example of a functional block diagram of the control unit of the recording device included in the biomagnetic measurement system according to an embodiment of the present invention.

FIG. 6 is an example of a functional block diagram of the control unit 70 of the recording device 13 included in the biomagnetic measurement system 1. As illustrated in FIG. 6, the control unit 70 includes a magnetic signal acquiring unit 710, an artifact confirming unit 720, and a current value adjusting unit 730, as the main functional blocks. The control unit 70 may include other functional blocks according to need.

The magnetic signal acquiring unit 710 has a function of acquiring, from the magnetic sensor 11, magnetic signals generated when a stimulation current is applied to the living body by the electrical stimulation apparatus 30, and storing the magnetic signals in the RAM 73, for example. Further, the magnetic signal acquiring unit 710 has a function of summing and averaging the magnetic signals acquired in synchronization with the electrical stimulation applied by the electrical stimulation apparatus 30.

The artifact confirming unit 720 confirms the magnitude of the artifact caused by the stimulation current. Specifically, the artifact confirming unit 720 has a function of confirming the magnitude of the artifact included in the magnetic signals acquired from the magnetic sensor 11 by the magnetic signal acquiring unit 710. Here, an artifact is a noise component outside objectives, mixed in the acquired magnetic signals.

The current value adjusting unit 730 has a function of controlling the electrical stimulation apparatus 30 to adjust the amplitude (pulse height) and time (pulse width) of the pulsed current generated by the electrical stimulation apparatus 30.

Figure 7:
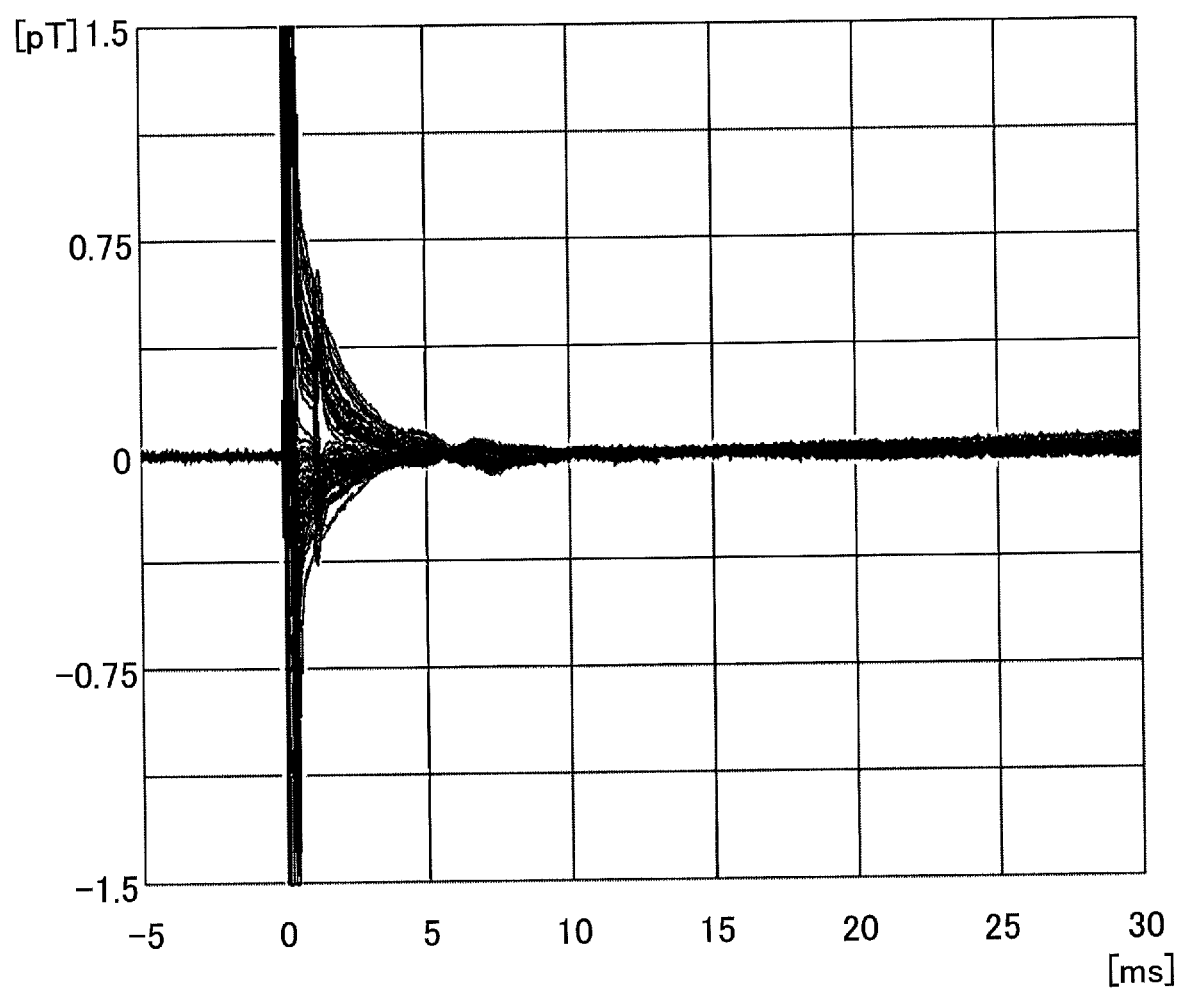
FIG. 7 is a diagram illustrating an example of magnetic signals obtained from a living body caused by a stimulation current of FIG. 4 according to an embodiment of the present invention.

For example, a case where the electrical stimulation apparatus 30 generates the pulsed stimulation current illustrated in FIG. 4 in a state where the electrode 40 is attached to the position of FIG. 2, and applies the pulsed stimulation current between the anode and cathode of the electrode 40, is considered. In this case, for example, the magnetic signals illustrated in FIG. 7 are obtained. In FIG. 7, magnetic signals obtained from a plurality of sensors are superimposed and displayed.

As illustrated in FIG. 7, electrical stimulation is applied at the time of 0 msec, and the artifact continues to approximately 7 msec. The magnetic signals, which are induced by the electrical stimulation applied by the electrical stimulation apparatus 30, appear from 3 msec to 13 msec, and, therefore, the first portion of the magnetic signals overlaps the artifact.

The generation of artifacts depends on the parasitic capacitance between the electrode 40 and the stimulating region of the subject 300. That is, upon applying electrical stimulation, electric charges are applied to the parasitic capacitance between the electrode 40 and the stimulating region of the subject 300. The current, which is generated when these electric charges diffuse at a predetermined time constant, results in magnetic noise (artifact), which adversely affects the biomagnetic measurement.

Figure 8:
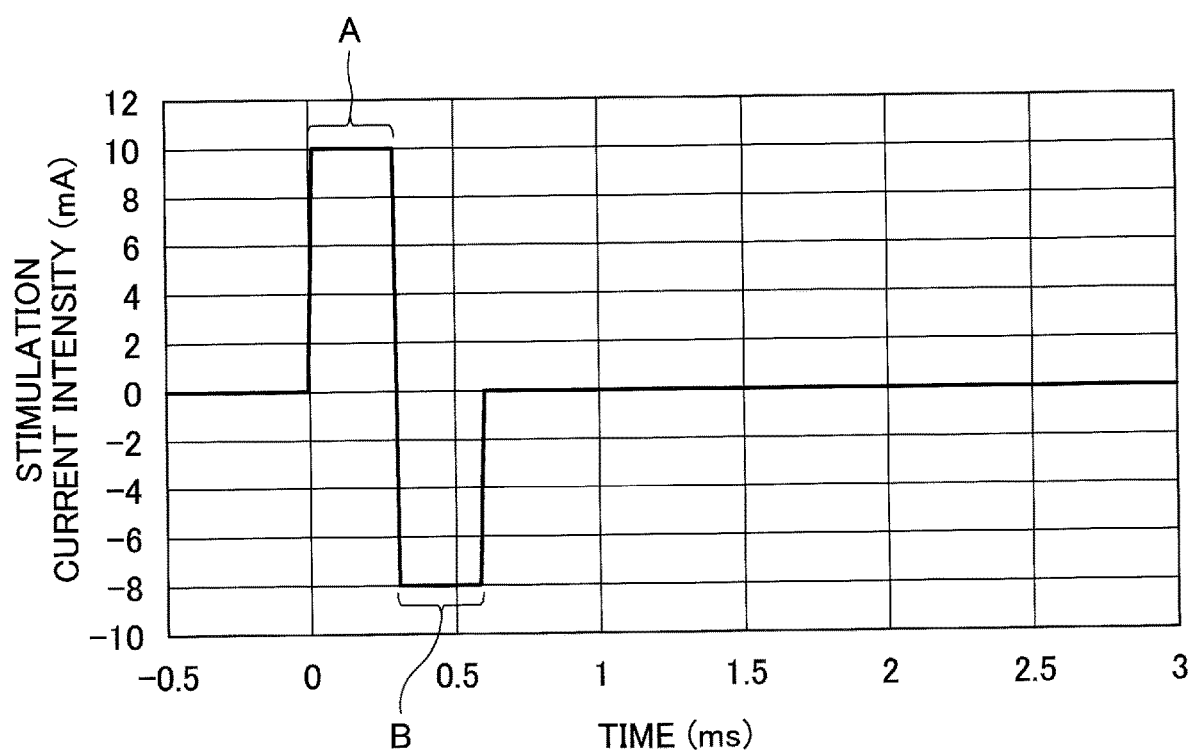
FIG. 8 is a diagram illustrating an example of an artifact compensation current that reduces artifacts according to an embodiment of the present invention.

FIG. 8 illustrates an example of an artifact compensation current that reduces the artifact. In FIG. 8, immediately after a stimulation current A is applied, an artifact compensation current B, which is a pulse signal having an opposite phase to that of the stimulation current A, is applied. This forces the withdrawal of the electric charges applied to the parasitic capacitance. As a result, the number of diffusing electric charges is reduced, and the adverse effects of artifacts can be reduced. This technique physically reduces the artifacts (i.e., without the use of the signal processing technique), and, therefore, a distortion in the biomagnetic signals, which would be caused in the case of performing signal processing, will not be caused in the case of performing this technique.

The amplitude and the pulse width of the artifact compensation current B do not have to be the same as the amplitude and the pulse width of the stimulation current A. That is, the amplitude of the artifact compensation current B can be adjusted independently of the amplitude of the stimulation current A, and the pulse width of the artifact compensation current B can be adjusted independently of the pulse width of the stimulation current A.

Figure 9:
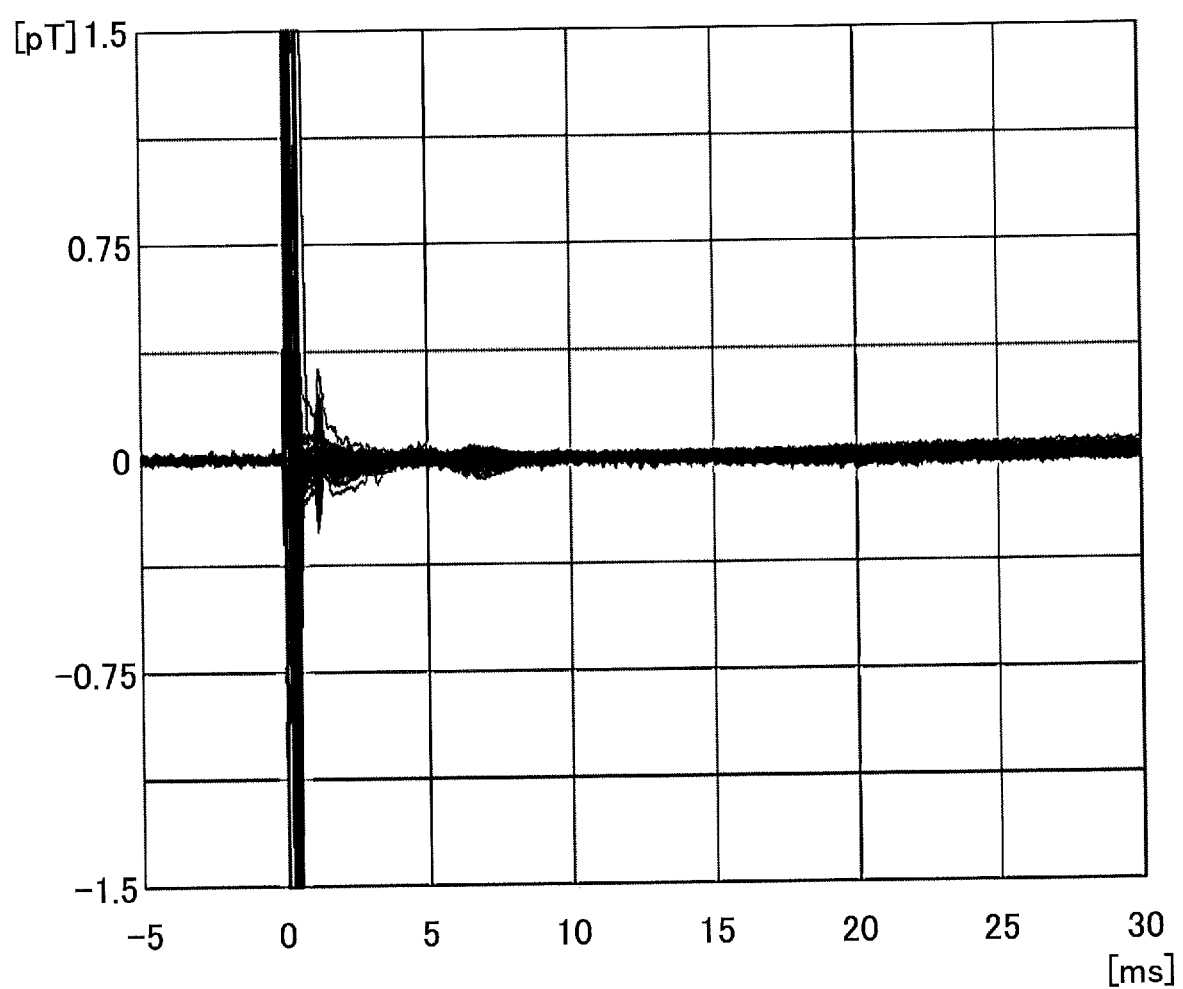
FIG. 9 is a diagram illustrating an example of magnetic signals obtained from a living body caused by a stimulation current and an artifact compensation current of FIG. 8 according to an embodiment of the present invention.

By adjusting the amplitude and the pulse width of the artifact compensation current B to appropriate values, the convergence of the artifact can be accelerated, making it easier to view the biomagnetic signals, as illustrated in FIG. 9. Compared to FIG. 7, the improvement effect is clear.

Figure 10:
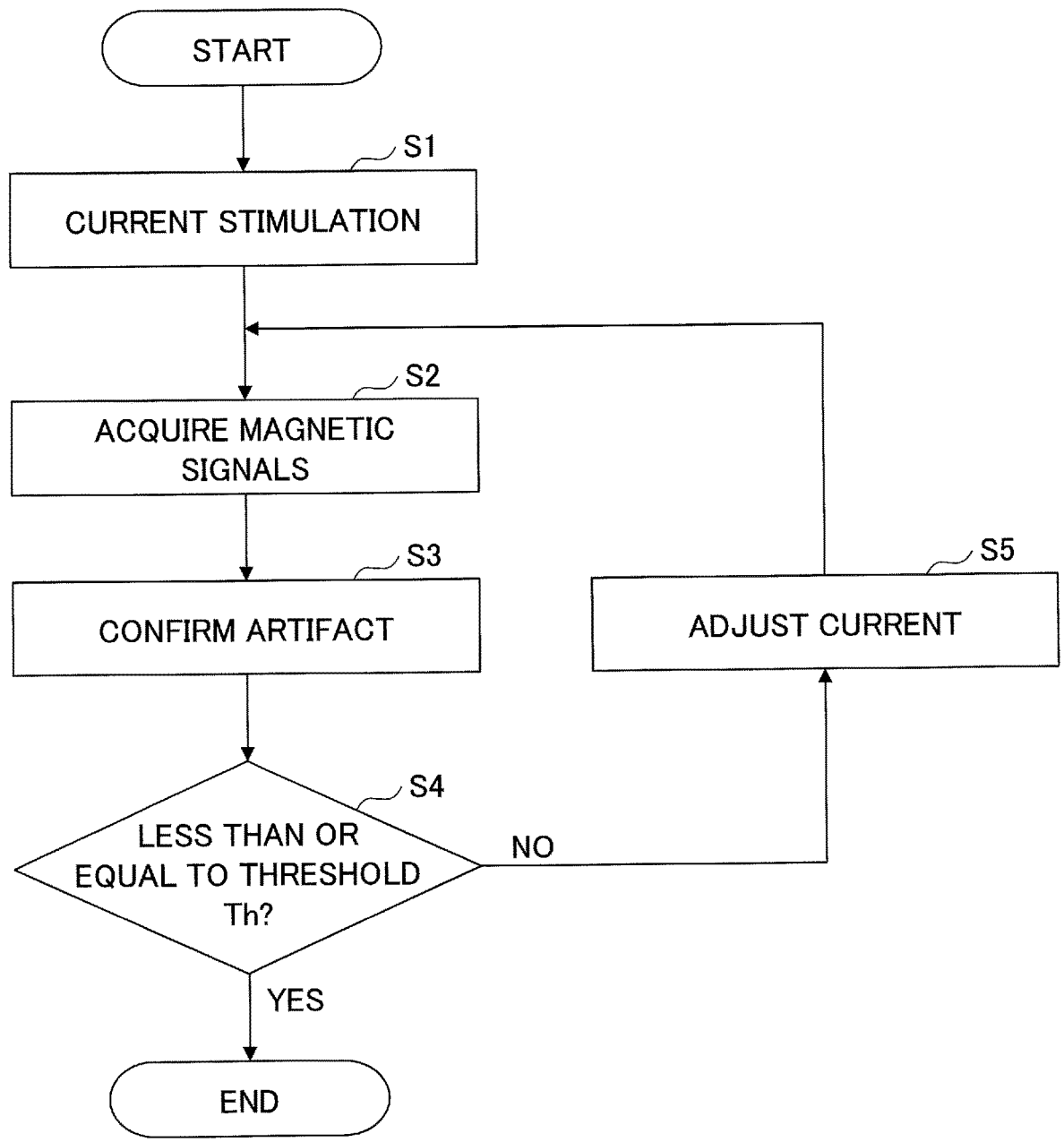
FIG. 10 is a flowchart illustrating an example of a biomagnetic measurement method according to an embodiment of the present invention.

FIG. 10 is a flowchart illustrating an example of a biomagnetic measurement method, and explains mainly the method of adjusting the artifact compensation current. First, in step S1, the current value adjusting unit 730 reads out the values of the amplitude and the pulse width of the artifact compensation current B stored in the RAM 73. Then, information corresponding to the stimulation current A (fixed value) and the waveform of the artifact compensation current B (for example, the waveform illustrated in FIG. 8) is input to the electrical stimulation apparatus 30, and the electrical stimulation apparatus 30 applies current stimulation to the subject. Note that the current value adjusting unit 730 may input information corresponding to the stimulation current A (for example, the waveform illustrated in FIG. 4) to the electrical stimulation apparatus 30, and the electrical stimulation apparatus 30 may apply current stimulation to the subject only by the stimulation current A.

Next, in step S2, the magnetic signal acquiring unit 710 acquires, from the magnetic sensor 11, the magnetic signals at the time of applying the current stimulation, and stores the magnetic signals in the RAM 73. At this time, the magnetic signal acquiring unit 710 may sum and average the magnetic signals acquired in synchronization with the electrical stimulation applied by the electrical stimulation apparatus 30.

Next, in step S3, the artifact confirming unit 720 reads out the magnetic signals acquired by the magnetic signal acquiring unit 710 from the magnetic sensor 11 and stored in the RAM 73, and confirms the magnitude of the artifact in the magnetic signals that have been read out. Specifically, for example, the artifact confirming unit 720 accumulates the values of the magnetic signals in a predetermined interval of the magnetic signals (for example, between 1 msec and 5 msec after the time when the electrical stimulation is applied).

Alternatively, the artifact confirming unit 720 may confirm the magnitude of the artifact based on the amplitude at a particular time (for example, between 1 msec and 5 msec after the time when the electrical stimulation is applied) of the magnetic sensor 11 of a particular channel. Further, the artifact confirming unit 720 may confirm the magnitude of the artifact based on the accumulated value in a predetermined interval (for example, between 1 msec and 5 msec after the time when the electrical stimulation is applied) of the magnetic sensor 11 of a particular channel. In these cases, the particular channel may be a single channel, multiple channels, or all of the channels.

Next, in step S4, the artifact confirming unit 720 determines whether the accumulated value of the magnetic signals is less than or equal to a predetermined threshold value Th.

When it is determined in step S4 that the accumulated value of the magnetic signals is greater than the predetermined threshold value Th (in the case of NO), the process proceeds to step S5. In step S5, the current value adjusting unit 730 adjusts the amplitude and/or the pulse width of the artifact compensation current B, and stores the value of the amplitude and/or the pulse width of the artifact compensation current B that has been adjusted in the RAM 73 (update the value in the RAM 73). Thereafter, the process returns to step S1 again and the same process as above is repeated.

When it is determined in step S4 that the accumulated value of the magnetic signals is less than or equal to the predetermined threshold value Th (in the case of YES), the adjustment of the artifact compensation current B is ended. In subsequent measurements, the values of the amplitude and the pulse width of artifact compensation current B that have been last stored value in the RAM 73, will be used.

As described above, in the biomagnetic measurement system 1, the artifact compensation current B can be automatically adjusted based on information from the artifact confirming unit 720. Note that the optimum values of the amplitude and the pulse width of the artifact compensation current B may be obtained in advance according to the flow in FIG. 10, and the values may be used as fixed values. In this case, the artifact compensation current B will not be automatically adjusted.

As described above, in the biomagnetic measurement system 1, the magnetic measurement apparatus 10 includes the artifact confirming unit 720 for confirming the magnitude of the artifact caused by the stimulation current from the electrical stimulation apparatus 30. Further, the electrical stimulation apparatus 30 can output the artifact compensation current B that reduces the artifact after the stimulation current A is output, based on the information from the artifact confirming unit 720.

By outputting the artifact compensation current B after the stimulation current A is output, the electric charges applied to the parasitic capacitance can be forcibly withdrawn, thereby reducing the number of diffusing electric charges and reducing the adverse effects of the artifact. By adjusting the amplitude and the pulse width of the artifact compensating current B to appropriate values, the convergence of the artifact can be accelerated, making it easier to view the biomagnetic signals. This technique physically reduces the artifact, and is thus preferable because a distortion in the biomagnetic signals, which would be caused in the case of performing signal processing, will not be caused in the case of performing this technique.

Note that the biomagnetic measurement system 1 can be used, for example, to measure magnetic fields from the spinal cord, peripheral nerves, muscles, and the brain, induced by electrical stimulation.

Modified Example of First Embodiment

A modified example of the first embodiment indicates a waveform of a stimulation current that is different from that of the first embodiment. Note that in the modified example of the first embodiment, descriptions of the same configuration portions as those of the previously described embodiment may be omitted.

It is preferable that the time from applying the stimulation current A to the end of the application of the artifact compensation current B that is applied after the stimulation current A, is less than or equal to 1 msec That is, the total time from the rise of the stimulation current A to the rise of the artifact compensation current B is preferably less than or equal to 1 msec. When the total time is less than or equal to 1 msec, the effect of forcibly withdrawing the electric charges applied to the parasitic capacitance, can be sufficiently exhibited.

Figure 11:
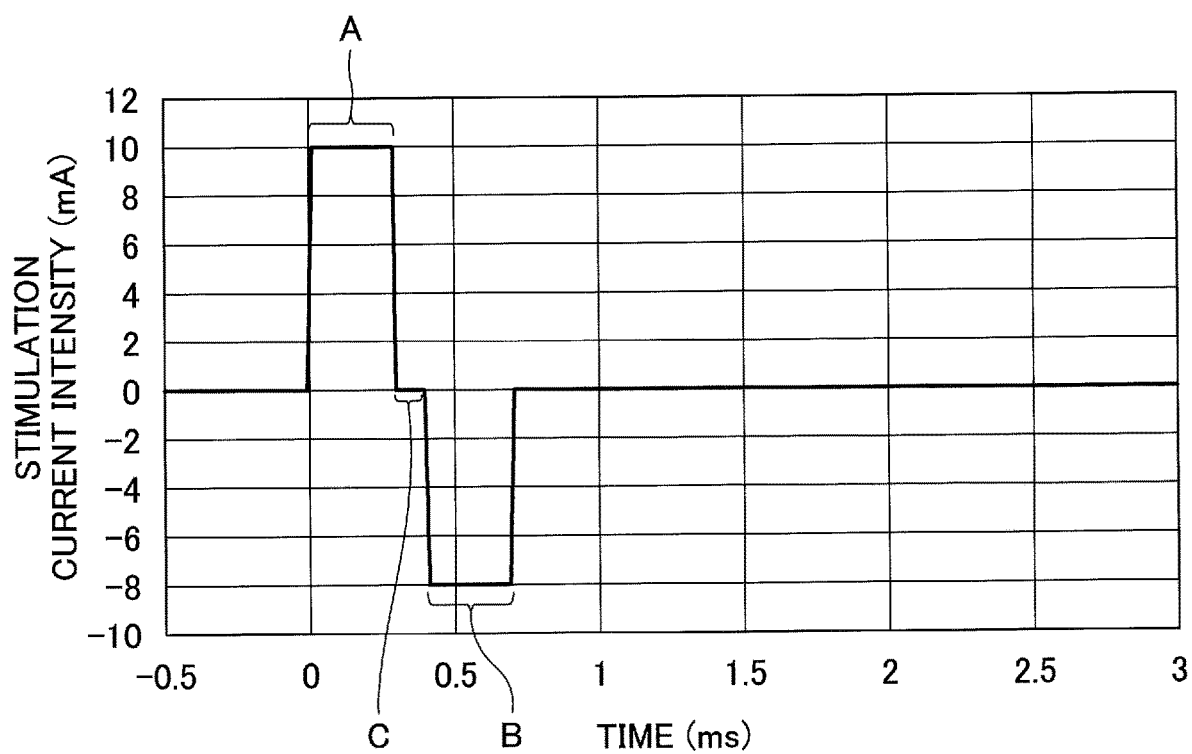
FIG. 11 is a diagram illustrating another example of an artifact compensation current according to an embodiment of the present invention.

As long as the total time is less than or equal to 1 msec, the current stimulation waveform is not limited to the waveform of FIG. 8, and may be, for example, the waveform such as that of FIG. 11. In FIG. 11, a time C during which a current is not applied, is set between the stimulation current A and the artifact compensation current B.

According to one embodiment of the present invention, a biomagnetic measurement system that is capable of physically reducing artifacts, can be provided.

The biomagnetic measurement system and the biomagnetic measurement method are not limited to the specific embodiments described in the detailed description, and variations and modifications may be made without departing from the spirit and scope of the present invention.

What is claimed is:

1. A biomagnetic measurement system comprising:
a magnetism measurement apparatus configured to measure a magnetism of a target; and
an electrical stimulation apparatus configured to apply a stimulation current to the target, wherein
the magnetism measurement apparatus includes:
a processor configured to confirm a magnitude of an artifact caused by the stimulation current, wherein
the electrical stimulation apparatus is configured to output a compensation current for reducing the artifact after the stimulation current is output, based on information from the confirming unit,
wherein an elapsed time from a time to start applying the stimulation current to a time to stop outputting the compensation current is equal to or less than a first predetermined time, and
wherein the first predetermined time is 1.0 msec.

2. The biomagnetic measurement system according to claim 1, wherein the electrical stimulation apparatus is configured to automatically adjust the compensation current based on the information from the processor.

3. The biomagnetic measurement system according to claim 1, wherein the magnetism measurement apparatus further includes:
a magnetic sensor,
wherein the processor is further configured to
acquire, from the magnetic sensor, magnetic signals generated when the stimulation current is applied, and
confirm the magnitude of the artifact included in the magnetic signals.

4. The biomagnetic measurement system according to claim wherein the magnetic signals are summed and averaged.

5. The biomagnetic measurement system according to claim 1, wherein the stimulation current and the compensation current are pulse signals having opposite phases to each other.

6. The biomagnetic measurement system according to claim 1, wherein neither the stimulation current nor the compensation current is applied for a second predetermined time within the elapsed time.

7. A biomagnetic measurement method comprising
applying a stimulation current to a target;
confirming a magnitude of an artifact caused by the stimulation current; and
outputting a compensation current for reducing the artifact after the stimulation current is output, based on information obtained at the confirming,
wherein an elapsed time from a time to start applying the stimulation current to a time to stop outputting the compensation current is equal to or less than a first predetermined time, and
wherein the first predetermined time is 1.0 msec.

* * * * *